United States Patent [19]
Schneider et al.

[11] Patent Number: 5,417,677
[45] Date of Patent: May 23, 1995

[54] FLUSHABLE PH-SENSITIVE OSTOMY POUCH CONTAINING ITS OWN PH-MODIFIER

[75] Inventors: Barry L. Schneider, McHenry; Claudio Giori, Riverwoods, both of Ill.

[73] Assignee: Hollister Incorporated, Libertyville, Ill.

[21] Appl. No.: 248,519

[22] Filed: May 24, 1994

[51] Int. Cl.$^6$ ............................................. A61F 5/44
[52] U.S. Cl. ....................................................... 604/332
[58] Field of Search .................................. 604/332–338

[56] References Cited

U.S. PATENT DOCUMENTS

| | | | |
|---|---|---|---|
| 4,543,097 | 9/1985 | Polen | 604/333 |
| 4,762,738 | 8/1988 | Keyes et al. | 604/332 |
| 4,826,493 | 5/1989 | Martini et al. | 604/333 |
| 5,108,382 | 4/1992 | Wright | 604/342 |
| 5,110,390 | 5/1992 | Martini et al. | 604/338 |

FOREIGN PATENT DOCUMENTS 8404036 10/1984 WIPO .

*Primary Examiner*—Jerome L. Kruter
*Attorney, Agent, or Firm*—Tilton Fallon Lungmus

[57] ABSTRACT

A flushable ostomy pouch having side walls composed of pH-sensitive material capable of dissolving when exposed to an aqueous fluid having a pH substantially above or below a neutral pH level, and containing a quantity of pH-modifying material to initiate dissolution of the pouch when it is discarded in the water of a toilet bowl, is disclosed. The pouch includes a pair of side walls and an external membrane that extends along at least one of the side walls to define a pocket adjacent to that side wall. A quantity of pH-modifying material is contained in the pocket which, when exposed to a generally pH-neutral fluid entering the pocket, is capable of changing the pH of the fluid in the pocket to a level above or below the neutral pH level. The external membrane is formed such that, when the pouch is discarded in a toilet bowl, it allows aqueous fluid to enter the pocket and contact or dissolve the pH-modifying material, thereby causing the fluid entering the pocket to attain a pH substantially above or below the neutral pH level and dissolve the pH-sensitive side wall adjacent to the membrane.

12 Claims, 1 Drawing Sheet

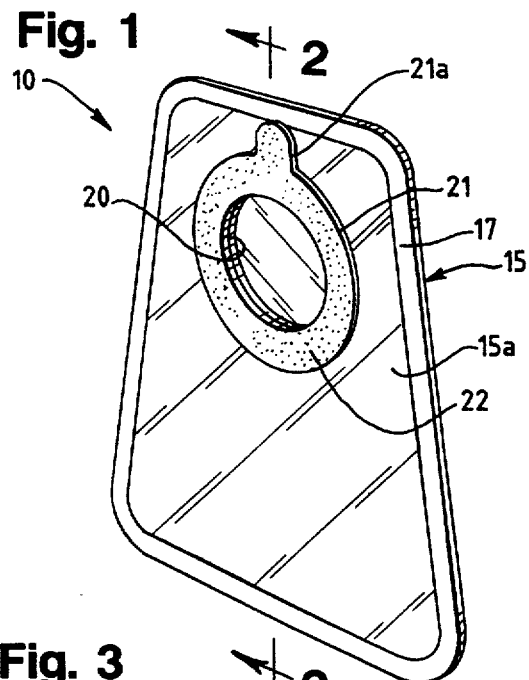
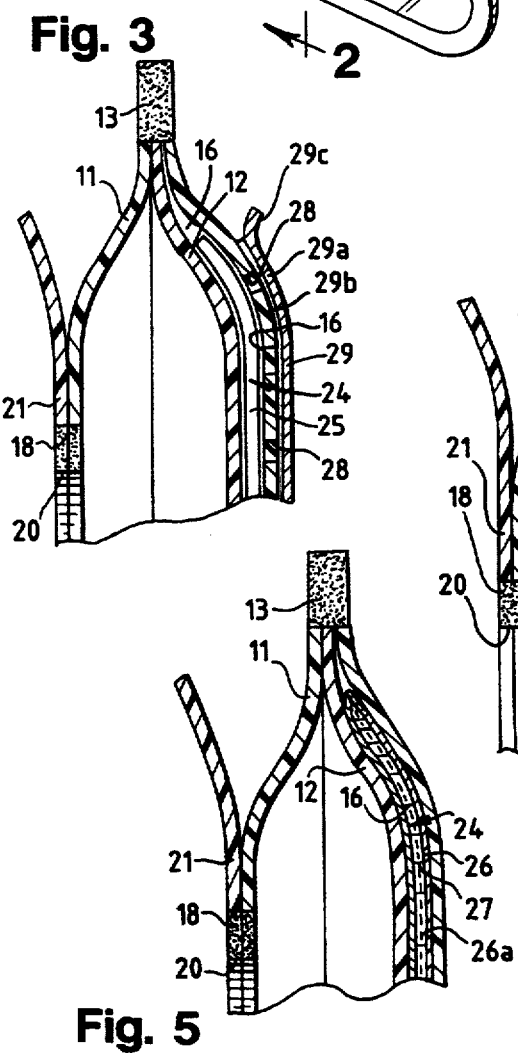
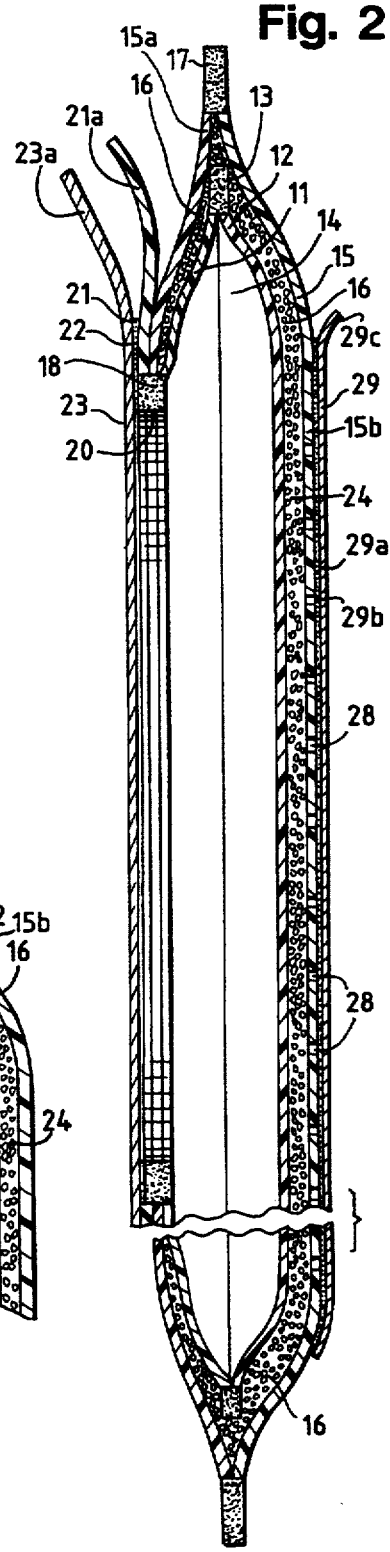

FLUSHABLE PH-SENSITIVE OSTOMY POUCH CONTAINING ITS OWN PH-MODIFIER

BACKGROUND AND SUMMARY

Soluble ostomy pouches are known in which the pouch may be discarded and dissolved (or dispersed) in the water of a common toilet bowl and in the discharge lines of a waste-disposal system. One type of such a pouch is constructed of a pair of side walls that are each composed of at least two layers, specifically, a tough, flexible, but water-soluble or water-dispersible primary layer, which gives the pouch its structural integrity and a thin, water-insoluble layer which lines the inside of the pouch and prevents the pouch's contents from contacting and dissolving the primary layer when the pouch is worn (see U.S. Pat. Nos. 4,772,279 and 4,917,689). Another type of known flushable pouch is at least partially formed of pH-sensitive material so that a basic or acidic agent may be added to the toilet bowl to initiate dissolution of the pouch (see U.K. patent application GB 2,201,372A and U.S. Pat. No. 4,629,999). While such pouches may be discarded in a toilet bowl and through the discharge lines of a water-disposal system, such constructions have not been entirely successful because of manufacturing complexities and user inconvenience. In particular, regarding the laminate construction of a water-soluble primary layer with a water-insoluble protective liner, manufacturing such a construction has proven to be difficult and problems may also be encountered with the water-soluble primary layer prematurely dissolving while the pouch is being worn. Regarding pH-sensitive pouches for which it has been proposed to add a basic or acidic agent to the toilet bowl to initiate dissolution of the pouch, it has been found that relatively large quantities of such agents are required to alter the pH of the water in the entire toilet bowl to the pH level required to disintegrate the pouch, and users of such devices find carrying such large quantities, in some instances of highly caustic material, inconvenient and possibly dangerous.

The present invention is concerned with a pouch constructed of pH-sensitive materials but, as mentioned, it is believed impractical, as in prior systems, to change the pH of the entire volume of water in a toilet bowl to a level sufficient to dissolve the pouch, as this would require the user to carry large quantities of acid-forming or base-forming agents which may be dangerous. Carrying such large quantities of pH-modifying material is inconvenient in that it requires the user to carry separate components and involves the additional step of adding that substance to the toilet bowl. Obviously, requiring the user to carry and add such pH-modifying materials, which may be caustic and dangerous, is contrary to the objectives of providing a convenient, toilet bowl disposable ostomy pouch.

An important aspect of this invention therefore lies in providing a self-contained, flushable, pH-sensitive ostomy pouch that includes its own pH-modifiers so that it will readily disintegrate when discarded in the water of a toilet bowl without requiring a user to carry and add additional components to the toilet bowl water to initiate dissolution of the pouch. Such an ostomy pouch comprises a pair of side walls joined together along their outer margins and composed of pH-sensitive material capable of dissolving when exposed to an aqueous fluid having a pH substantially above or below a neutral pH level. An external membrane is secured to the pouch and extends adjacent to at least one of the side walls to define a pocket therebetween. A quantity of pH-modifying material is contained in the pocket which, when exposed to a generally pH-neutral fluid entering the pocket, is capable of changing the pH of the fluid in the pocket to a level substantially above or below a neutral pH. If the pouch walls are sensitive to fluids of elevated pH and alkali-soluble, the pH-modifying material may take the form of a finely-divided, dry alkali material which is only relatively caustic and is fully hydrated so that it will not draw moisture through the external membrane when the pouch is being worn. Dry, finely-divided sodium metasilicate pentahydrate has been found to be particularly effective for this purpose. Alternatively, a tissue layer impregnated with such a dry base-forming material may be disposed in the pocket. Such a tissue layer is believed to be highly effective in enhancing the rate of dissolution of the pouch walls as its hydrophilic and absorbent nature, when exposed to water in a toilet bowl, tends to draw water into the pocket and maintain that water, of elevated pH, in close contact with the pouch side walls. If the pouch walls are sensitive to fluids of lowered pH, suitable acid-forming agents may be contained in the pocket or impregnated into a tissue layer disposed in the pocket.

The external membrane includes an entrance means for allowing aqueous fluid to enter the pocket and contact or dissolve the pH-modifying material when the pouch is discarded in the water of a toilet boil. Once the fluid entering the pocket dissolves or mixes with the pH-modifying material and attains an elevated or lowered pH, it initiates dissolution of the pouch by dissolving the adjacent pouch wall or walls such that the pouch loses its structural integrity and may be safely and effectively flushed away through the discharge lines of the waste-disposal system.

In one embodiment, the external membrane is composed of pH-sensitive material and the entrance means may take the form of a plurality of apertures in the membrane. A strip of removable adhesive tape is used to cover the apertures while the pouch is being worn, and a user removes the adhesive tape prior to discarding the pouch in the water of a toilet bowl. When the pouch is so discarded, aqueous fluid in the toilet bowl flows through the apertures and contacts or dissolves the pH-modifying material, which changes the pH level of the fluid now within the pocket to a level substantially above or below a neutral pH level. The fluid of altered pH then dissolves the adjacent pouch walls as well as the pH-sensitive external membrane.

In another embodiment, the external membrane is composed of a water-soluble polymeric material, such as polyvinyl alcohol, which is capable of quickly dissolving or dispersing in the water of a toilet bowl. Such a water-soluble external membrane acts as the entrance means for allowing aqueous fluid to enter the pocket because, when the membrane is exposed to water in a toilet bowl, the water will initiate disintegration of the membrane and enter the pocket where it contacts the pH-modifying material and attains an altered pH level. In a similar construction, the external membrane may be composed of a water-sensitive cellulosic material such as tissue paper which is capable of quickly dissolving or dispersing in the water of a toilet bowl. When the pouch is discarded in the water of a toilet bowl, the tissue paper allows water to pass therethrough and contact or dissolve the pH-modifying material in the pocket, which results in the fluid attaining an altered pH and dissolving the adjacent pouch walls. In such embodiments, the pouch is preferably contained in a soft cloth comfort pack while it is being worn to shield the water-soluble external membrane from direct contact with the user's skin; otherwise, moisture from the skin's surface might cause premature disintegration of the water-soluble membrane.

In some embodiments, it may be desirable to use a liquid as the pH-modifying material. Common basic or acidic liquids may be used but it is believed that liquid ammonia is particularly effective in such cases. In such an embodiment, the liquid agent is contained in a rupturable packet that is disposed in the pocket between the external membrane and the pouch side walls. The rupturable packet, preferably made of a foil material, includes lines of weakness which, when the packet is squeezed between a user's fingers, will rupture and thereby cause the liquid contained therein to be dispersed throughout the pocket. The pouch is then discarded in the water of a toilet bowl.

In the preferred embodiments, the pouch side walls are formed of alkali-sensitive materials, such as alkali-soluble carboxylated acrylic polymers, capable of dissolving when exposed to an aqueous fluid having a pH level higher than approximately 10. In such embodiments, the pocket defined by the external membrane and the pouch side walls acts as a means for localizing and concentrating fluid of elevated pH in close proximity to the alkali-soluble pouch walls so that only the fluid in the pocket must attain a pH level above 10 to result in dissolution of the adjacent pouch walls. Since the pocket has a relatively small volume of about 5 to 20 milliliters, preferably about 10 milliliters, only a minute quantity of sodium metasilicate pentahydrate or a like material is required to elevate the pH level of the fluid in the pocket to approximately 11 (the approximate pH level required to initiate dissolution of the pouch side walls). Such a construction is particularly advantageous as the user is not required to carry any additional agents or components to facilitate dissolution of the pouch and the pouch itself only requires a relatively limited amount of pH-modifying material to dissolve the pouch such that it may be safely and effectively flushed away through a toilet bowl and waste-disposal system.

Other advantages, features and objects of the invention will become apparent from the specification and drawings.

BRIEF DESCRIPTION OF DRAWINGS

FIG. 1 is a perspective view of an ostomy pouch embodying this invention.

FIG. 2 is an enlarged, somewhat schematic cross-sectional view of one embodiment of the pouch of this invention.

FIG. 3 is an enlarged, somewhat schematic cross-sectional view illustrating another embodiment of this invention.

FIG. 4 is an enlarged, somewhat schematic cross-sectional view illustrating another embodiment of this invention.

FIG. 5 is an enlarged, somewhat schematic cross-sectional view illustrating another embodiment of this invention.

DETAILED DESCRIPTION OF PREFERRED EMBODIMENTS

In FIGS. 1 and 2, the numeral 10 generally designates an ostomy pouch having a pair of side walls 11 and 12 joined together along their outer margins by a marginal heat seal 13 or other suitable means to form an interior chamber 14. An external membrane 15 is secured to the pouch side walls and defines a pocket 16 between the external membrane and a substantial portion of the outer surfaces of the pouch side walls. In the illustrations given in FIGS. 1 and 2, external membrane 15 includes a first panel 15a that extends adjacent to side wall 11 and a second panel 15b that extends adjacent to side wall 12. Panels 15a and 15b are joined together about their periphery by marginal heat seal 17 or other suitable means. In alternate constructions, heat seal zones 13 and 17 may coincide. Panel 15a is also joined by a heat seal at 18 to side wall 11. It will be understood that external membrane 15 may define a pocket 16 adjacent to only one of the pouch side walls or only a portion of one of the side walls. For example, as illustrated in FIGS. 3-5, external membrane 15 may include only one panel 15b that extends along side wall 12 and is secured to that side wall with marginal heat seal 13, which also joins side walls 11 and 12. Depending upon the particular embodiment, the volume of pocket 16 will vary as discussed in more detail hereinafter.

Side wall 11 of the pouch has an opening 20 therethrough which defines a side opening or stoma receiving opening for the pouch. In the construction shown in FIGS. 1 and 2, opening 20 also passes through panel 15a of external membrane 15. In the illustrations given, pouch 10 is one component of a two-piece ostomy appliance, the other component being an adhesive faceplate (not shown) that may be adhesively secured to the peristomal skin surfaces of a patient. An external mounting ring 21 circumscribes the pouch opening and is coated along its outer surface (i.e., the surface facing away from the pouch) with an annular layer 22 of pressure sensitive adhesive. Mounting ring 21 is secured to the other layers around opening 20 by annular heat seal 18. A removable release sheet 23 of siliconized paper (shown only in FIG. 2) covers adhesive coating 22 until use, such sheet preferably having a pull tab 23a to facilitate such removal. Mounting ring 21 may be provided with one or more peripheral extensions or tabs 21a which project radially outward beyond the remaining periphery of the mounting ring so that a user may readily grip the tab as the pouch is being manipulated to secure the mounting ring to the faceplate or detach it from that faceplate. A particularly effective faceplate component, which includes a smooth annular surface for sealingly engaging the adhesive layer 22 of ring 21 and has a protective annular flange for guiding the ring onto the faceplate and covering the exposed edges of the pouch walls around opening 20, is disclosed in co-owned pending application Ser. No. 042,008. It is to be understood that while pouch 10 has been shown and described as one component of a two-piece appliance, it may instead constitute the sole element of a one-piece appliance, in which case mounting ring 21 would constitute an integrated faceplate for direct adhesive attachment to the peristomal skin surfaces.

Side walls 11, 12 are composed of a pH-sensitive material capable of dissolving when exposed to an aqueous fluid having a pH substantially above or below a neutral pH level. While the present invention contemplates constructing the pouch walls of materials that dissolve when exposed to an aqueous fluid having a pH lower than a neutral pH level, it is believed preferable to form the side walls of materials that are alkali-sensitive and capable of dissolving upon contact with an aqueous fluid having a pH higher than approximately 10. Particularly effective materials for constructing the pouch side walls are alkali-soluble carboxylated acrylic polymers or styrene-acrylic copolymers. It will be noted that, although side walls 11, 12 are illustrated as having only one layer, side walls 11, 12 may be comprised of multiple layers such as an outer layer of alkali-soluble material and an inner, thin film or coating of a water-insoluble polymer such as polyvinylidene chloride or copolymers thereof. Such a water-insoluble inner coating may be particularly desirable when the primary structural layer is composed of a blend of pH-sensitive and water-soluble materials to prevent the contents of the pouch from causing premature dissolution of the pouch walls. Regardless of the particular material used for constructing side walls 11, 12, the pouch side walls should be capable of sufficiently dissolving (or dispersing), when exposed to an aqueous fluid or elevated or lowered pH, so that the pouch may be safely and effectively flushed away through a common toilet bowl and the discharge lines of a waste-disposal system.

A quantity of pH-modifying material, generally designated at 24, is contained in pocket 16 and when exposed to a generally pH-neutral fluid entering the pocket, material 24 is capable of changing the pH of the fluid in the pocket to a level substantially above or below a neutral pH level. The particular pH-modifying material used will depend upon the construction and sensitivity of side walls 11, 12. Material 24 may be composed of a dry, finely-divided, water-soluble material (FIGS. 2 and 4) which is capable of forming an acid or base when mixed with water. The dry material should be only mildly caustic and fully hydrated so that it will not draw moisture through the external membrane when the pouch is in storage or being worn. An alkali metal salt such as hydrated sodium metasilicate has been found to be particularly effective, but other pH-modifying agents that are not highly hygroscopic and strongly caustic may be used. Examples of other such pH-modifying agents include trisodium phosphate dodecahydrate and sodium carbonate.

As illustrated in FIG. 3, pH-modifying material 24 may also take the form of a tissue layer 25 that is impregnated with a base-forming or acid-forming material. Impregnating such a material into tissue layer 25 is advantageous as the highly absorbent and hydrophilic nature of the tissue layer, when exposed to water in a toilet bowl, tends to draw water into pocket 16 and then maintain that water (having an altered pH) in close contact with the pouch side walls, thereby enhancing the dissolution of the pH-sensitive side walls. Such a tissue layer is also believed to be effective, when the toilet is flushed, in entrapping dispersed polymeric fragments of the pouch and pulling such fragments, which may tend to float, into the discharge lines of the waste-disposal system.

In the illustration given in FIG. 5, pH-modifying material 24 takes the form of a rupturable packet 26 that is disposed in pocket 16 and contains a quantity of pH-modifying liquid 27. Rupturable packet 26 is preferably made of a foil material and includes imperforate lines of weakness 26a which, when packet 26 is squeezed between a user's fingers, will rupture and allow liquid 27 to be dispersed throughout pocket 16. When the pouch is then discarded in the water of a toilet bowl, the fluid in the bowl enters pocket 16 and mixes with liquid 27 to attain an altered pH level. The fluid then disperses throughout the pocket and dissolves the adjacent pouch side walls. While liquid 27 may be composed of various acid-forming or base-forming materials, liquid ammonia has been found to be particularly effective for initiating dissolution of a pouch composed of alkali-soluble materials. In such a construction, packet 26 should contain approximately 5 to 20 milliliters of liquid ammonia, preferably about 10 milliliters, which is a sufficient amount to alter the pH of the fluid in the pocket to a level above approximately 10.

External membrane 15 is provided with entrance means for allowing aqueous fluid to enter pocket 16 and contact or dissolve pH-modifying material 24 when the pouch is discarded in the water of a toilet bowl. Such entrance means allow fluid to enter the pocket and attain, when it contacts the pH-modifying material, a pH substantially above or below a neutral pH level, thereby resulting in the fluid of altered pH dissolving the adjacent pouch walls. In one embodiment, the entrance means may take the form of a plurality of apertures 28 formed in membrane 15 (FIGS. 2 and 3). A strip of removable adhesive tape 29 having a backing layer 29a and a layer of pressure-sensitive adhesive 29b is adhesively secured over apertures 28 while the pouch is in storage and being worn. When it is desired to discard the pouch in a toilet bowl, the user removes tape 29 immediately prior to discarding the pouch in the toilet bowl and extended portion 29c is provided to facilitate such removal. In such an embodiment, external membrane 15 is preferably composed of the same pH-sensitive material as that of pouch walls so that the fluid of elevated pH will dissolve external membrane 15 as well as the adjacent pouch walls.

In other embodiments, illustrated in FIGS. 4 and 5, external membrane 15 may be composed of a water-soluble polymeric material such as polyvinyl alcohol or the like which will dissolve or disperse when exposed to water in a toilet bowl. In such a construction, the entrance means takes the form of the water-soluble polymeric layer which, when exposed to the water in the toilet bowl, allows aqueous fluid in the toilet bowl to flow into pocket 16. In a similar construction, external membrane 15 may be composed of a water-soluble cellulosic material such as a dissolvable paper or a water-dissolvable (or dispersible) tissue paper such as commonly used for toilet tissue and toweling. It will be noted that such cellulosic materials should probably not be used when the pH-modifying material takes the form of rupturable packet 26 as the liquid contained therein, when the packet is ruptured, might seep through the membrane and contact the user. In a construction where external membrane 15 takes the form of a water-soluble material, the pouch is preferably worn while it is placed in a soft cloth comfort pouch which encases the ostomy pouch and prevents direct contact between the water-soluble external membrane and the patient's skin; otherwise, moisture from the skin's surfaces might cause premature dissolution of the external membrane or might result in the pH-modifying material contacting the patient's skin.

In the present invention, the pocket defined by the external membrane and the pouch walls provides a means for localizing and concentrating fluid of altered pH in close proximity to the pH-sensitive pouch walls such that the pH of only the fluid in the pocket needs to be altered to initiate dissolution of the pouch. Hence, only a relatively limited quantity of pH-modifying material is required to dissolve the pouch such that it may be safely and effectively flushed away. The volume of pocket 16 will vary depending upon particular size and construction of the pouch, but it is believed that the pocket 16 should preferably have a volume of approximately 5 to 20 milliliters, with a volume of approximately 10 milliliters being preferred. The pouch is preferably formed of alkali-soluble materials that will dissolve upon contacting a fluid having a pH above approximately 10, and the pH-modifying material is preferably a dry, finely-divided base such as sodium metasilicate pentahydrate. In such an embodiment, if the pocket has a volume of about 10 milliliters, only about 0.005 grams of sodium metasilicate pentahydrate are required to elevate the pH of the fluid that enters the pocket to a pH-level of 11. Such fluid of elevated pH then dissolves the adjacent alkali-soluble pouch walls (and the external membrane when it is also constructed of an alkali-soluble material). While it will be understood that the volume of the pocket and the amount of pH-modifying material disposed therein may vary considerably, using an external membrane to define a pocket adjacent to the pouch walls results in a construction that requires only a relatively limited amount of pH-modifying material to initiate dissolution of the pouch so that it may be safely and effectively flushed away.

While in the foregoing, embodiments of the invention have been disclosed in considerable detail for purposes of illustration, it will be understood by those skilled in the art that many of these details may be varied without departing from the spirit and scope of the invention.

What is claimed is:

1. A flushable ostomy pouch comprising
   a pair of side walls joined together along their outer margins and composed of pH-sensitive material which will dissolve when exposed to an aqueous fluid having a pH substantially above or below a neutral pH level;
   an external membrane secured to said pouch and extending adjacent to at least one of said side walls to define a pocket therebetween; and
   a quantity of pH-modifying material contained in said pocket, said material, when exposed to water of generally neutral pH entering said pocket, acting to change said pH of said water in said pocket to a level substantially above or below said neutral pH level;
   said external membrane including entrance means for allowing toilet bowl water to enter said pocket and contact said pH-modifying material when said pouch is discarded into the bowl of a flush toilet, thereby causing the water entering said pocket to attain a pH substantially above or below said neutral pH level and dissolve the wall adjacent to said membrane.

2. The pouch of claim 1 in which said external membrane is formed of said pH-sensitive material and said entrance means comprises a plurality of apertures formed in said external membrane.

3. The pouch of claim 2 in which said apertures of said external membrane are covered by removable adhesive tape.

4. The pouch of claim 1 in which said external membrane comprises a water-soluble polymeric material capable of quickly dissolving in the water of a toilet bowl in which the pouch is discardable and said entrance means comprises said water-soluble polymeric material.

5. The pouch of claim 1 in which said external membrane comprises a water-soluble tissue layer capable of quickly dissolving in the water of a toilet bowl in which the pouch is discardable and said entrance means comprises said water-soluble tissue layer.

6. The pouch of claim 1 in which said pH-modifying material comprises a dry, finely-divided alkali metal salt.

7. The pouch of claim 1 in which said pH-modifying material comprises a tissue layer impregnated with a dry, finely-divided alkali metal salt.

8. The pouch of claim 1 in which said pocket has a volume of approximately 10 ml.

9. The pouch of claim 1 in which said quantity of said pH-modifying material comprises approximately 0.005 grams of sodium metasilicate pentahydrate.

10. The pouch of claim 1 in which said pH-modifying material comprises a rupturable packet containing a quantity of liquid pH-modifying material.

11. The pouch of claim 10 in which said quantity of liquid pH-modifying material comprises liquid ammonia.

12. The pouch of claim 11 in which said rupturable packet contains approximately 10 milliliters of said liquid ammonia.

* * * * *